(12) United States Patent
Larsen et al.

(10) Patent No.: US 7,004,010 B2
(45) Date of Patent: Feb. 28, 2006

(54) METHOD AND DEVICE FOR DETERMINING PENETRATION OF GASEOUS SUBSTANCE THROUGH A MEMBRANE

(75) Inventors: Hanne Larsen, As (NO); Achim Kohler, As (NO)

(73) Assignee: Difftech AS, As (NO)

( * ) Notice: Subject to any disclaimer, the term of this patent is extended or adjusted under 35 U.S.C. 154(b) by 0 days.

(21) Appl. No.: 10/501,466

(22) PCT Filed: Jan. 18, 2002

(86) PCT No.: PCT/NO02/00025

§ 371 (c)(1),
(2), (4) Date: Jul. 14, 2004

(87) PCT Pub. No.: WO03/060485

PCT Pub. Date: Jul. 24, 2003

(65) Prior Publication Data

US 2005/0076705 A1   Apr. 14, 2005

(51) Int. Cl.
G01N 15/08 (2006.01)
(52) U.S. Cl. ........................................... 73/38
(58) Field of Classification Search ............... 73/38, 73/52, 23.35, 23.36
See application file for complete search history.

(56) References Cited

U.S. PATENT DOCUMENTS

| 4,112,739 | A | * | 9/1978 | Lyssy | 73/38 |
| 4,854,157 | A | | 8/1989 | Wilson | |
| 4,864,845 | A | * | 9/1989 | Chandler et al. | 73/38 |
| 4,944,180 | A | * | 7/1990 | Tou et al. | 73/38 |
| 5,099,679 | A | * | 3/1992 | Huerlimann et al. | 73/19.06 |
| 5,131,261 | A | * | 7/1992 | Tou et al. | 73/38 |
| 5,212,933 | A | * | 5/1993 | Cere' | 53/556 |
| 5,347,845 | A | * | 9/1994 | Kepler | 73/31.03 |
| 5,361,625 | A | | 11/1994 | Ylvisaker | |
| 6,335,202 | B1 | * | 1/2002 | Lee et al. | 436/161 |
| 6,422,063 | B1 | * | 7/2002 | Anantheswaran et al. | 73/38 |
| 6,598,463 | B1 | * | 7/2003 | Sharp et al. | 73/38 |
| 6,684,684 | B1 | * | 2/2004 | Regimand et al. | 73/38 |
| 2002/0162384 | A1 | * | 11/2002 | Sharp et al. | 73/38 |

FOREIGN PATENT DOCUMENTS

| DE | 3724160 A1 | * | 2/1988 |
| EP | 0727655 | | 8/1996 |
| JP | 11030579 A | * | 2/1999 |
| WO | WO 00/09988 | | 2/2000 |

OTHER PUBLICATIONS

Larsen, et al "Ambient Oxygen Ingress Rate Method—An Alternative method . . . ", Packaging Technology and Science, 2000; 13:233-241.

(Continued)

Primary Examiner—Hezron Williams
Assistant Examiner—John Fitzgerald
(74) Attorney, Agent, or Firm—Christian D. Abel

(57) ABSTRACT

This invention relates to a method and device for measuring the penetration of gases through a package material. More specific, it relates to a method for predicting the transmission rate of the gaseous substance through the walls of a package as a function of time from a limited number of measured concentrations of the gaseous substance within the package. Even more specific, it relates to a method and device for testing the oxygen transmission rates into packages employed for instance for food or pharmaceutical products under realistic storing conditions.

7 Claims, 2 Drawing Sheets

OTHER PUBLICATIONS

Flodin et al, "oxygen permeance: a Method Applied to Modified Atmosphere Packages . . . ", Packaging Technology and Science, 1999; 12:185-191.

Demorest, "Recent Developments in Testing the Permeability of Good Barriers", J. Plastic Film & Sheeting, 1992, vol. 8, p. 109.

* cited by examiner

METHOD AND DEVICE FOR DETERMINING PENETRATION OF GASEOUS SUBSTANCE THROUGH A MEMBRANE

This invention relates to a method and device for measuring the penetration of gases through a package material. More specific, it relates to a method for predicting the transmission rate of a gaseous substance through the walls of a package as a function of time from a limited number of measured concentrations of the gaseous substance within the package. Even more specific, the invention relates to a method and device that is effective, versatile and relatively inexpensive for testing the oxygen transmission rates into packages employed for instance in the food and pharmaceutical industries.

BACKGROUND

Approximately 80% of all food products are sensitive towards loss or uptake of water vapour, flavours, and odours. These food products must therefore be stored in a protected environment from one or more of these gases. Especially oxygen can pose a serious problem since oxygen penetration into food packages are known to be detrimental to the flavour, texture, colour, nutrition, and/or shelf life of the food. Oxygen enters into many reactions which affect the shelf life of foods, e.g. microbial growth, colour changes in fresh and cured meats, oxidation of lipids and consequent rancidity, and senescence of fruit and vegetables. The shelf life of many foods is therefore determined by the oxygen transmission rate (OTR) of the material used to package the food, especially during long-term storage.

It is estimated that in 1991, more than 10 000 new food products were introduced in the US alone, a market where total sales amounted to billions of USD per year. Food products are typically sold in small units that often are individually packed. Thus the cost of the packaging material becomes a vital competition factor, and it has become increasingly important to find materials with an optimal balance between price and barrier properties against these gases.

This challenge has resulted in an increased use of barrier packages within the food industry, since they provide a cost efficient and practical manner of packaging food products while offering good protection from detrimental gases in the ambient air. The "barrier plastic" portion of the food packaging market is the fastest growing segment, and there is a world wide activity in achieving new and improved plastic barrier materials for food packaging, which can offer better protection against gas penetration and longer shelf life for a wide range of products.

As a result, there is a dramatic increase of the number and types of barrier plastic packages being made available for the package designers. The resultant challenge, then, is to quantify the demand of the food to be packed, and to match the proper barrier material to that particular application. Thus there is a growing demand for testing the barrier properties of package materials, especially for the oxygen transmission rate (OTR).

PRIOR ART

Normally in commercial testing of food packages, there is presently employed an isostatic ASTM-approved method of a dynamic permeation cell (flowing gas system) with a sensitive oxygen-specific coulometric detector. In this method, the oxygen penetration is determined by passing a gas stream with a known and pre-set oxygen-content on one side of a sheet of the packaging material and an oxygen-free gas on the other side and measuring the oxygen content in the latter gas stream after passing the packaging material. The method requires normalised conditions in order to give comparable results, and is usually performed at 23° C. and 0.50 or 0.75% relative humidity. Also, since the method measures the actual penetration of oxygen in real time through the barrier material, the oxygen sensor must necessarily be able to detect very dilute concentrations of oxygen. As a consequence, the detector becomes oversaturated and may be damaged if exposed to higher oxygen concentrations such as for instance in ordinarily air. When employing the method, care must be taken not to overexpose the oxygen sensor. Thus, the conventional method is cumbersome, expensive, and has a limited capacity such that it is usually restricted to testing packaging materials at non-realistic temperatures and air humidities.

It is known that both the temperature and air moisture affects the oxygen penetration through barrier materials [1]. Also, converting a flat material into a package usually changes the permeation due to effects such as stretching, heat-sealing, and eventual defects created during the conversion process [1]. Thus, there is a need for an efficient and reliable method that can determine the oxygen transmission rates into closed packages as a function of time under expected field temperature, barometric pressure, and relative humidity conditions.

OBJECTIVE OF THE INVENTION

The main objective of this invention is to provide a method and device for determining the transmission rate of a gaseous substance into a package as a function of time.

Another objective of this invention is to provide a method and device for determining of the oxygen transmission rate into packages under realistic field temperature, barometric pressure, and relative humidity conditions that can be expected for a wide variety of for instance food or pharmaceutical products.

DESCRIPTION OF THE INVENTION

The objectives of the invention can be obtained by what is given in the appended claims and the following description of the invention.

The following description of the invention will be directed towards the specific case of determining the oxygen transmission rate (OTR) into a food package. However, it should be understood that the inventive idea is of a general nature and can be employed for determining the penetration rates of any gaseous substance into any package, regardless which materials or dimensions that are involved.

The theoretical framework forming the basis for the inventive method is developed and thoroughly described in an article written by the inventors [2], and the article is enclosed in its entirety by reference. Here we will only give a brief summary:

In the case determining the oxygen transmission rates into a food package, one has that the partial pressure of oxygen within the package as a function of time can in general be given as:

$$\frac{dp}{dt} = -\kappa(p - p_0) \quad (1)$$

where κ is given by:

$$\kappa = D \cdot S \cdot \frac{A}{V \cdot L} \cdot k \cdot T \quad (2)$$

Here, $p_0$ is the partial pressure of oxygen in the ambient air, p is the partial pressure of oxygen within the package, t is time, D is the diffusion constant, S is the solubility coefficient, A is the surface area of the package, V is the volume of the package, L is the thickness of the barrier material, T is the temperature of the gas in the package, and k is the Boltzmann constant. The following assumptions are being made: Henry's law is valid to describe the absorption of oxygen on the outer surface (facing the ambient air) and the inner surface (facing the interior of the package) of the package material, Fick's law of diffusion describes the diffusion through bulk of the material, and the partial pressure of oxygen within the package is governed by the ideal gas law.

Thus, by integrating Eqn. (1) from a reference point ($p_1$, $t_1$) to point (p(t), t), one obtain the partial pressure of oxygen inside the package as a function of time:

$$p(t) = p_0 + (p_1 - p_0)e^{-\kappa(t-t_1)} \quad (3)$$

where $p_1$ is the partial oxygen pressure in the package measured at time $t_1$. Note that Eqn. (3) can be employed to determine κ from only two measurements of the partial pressure of oxygen inside the package, since by applying Eqn. (3) for two different measurements gives that:

$$\kappa = \frac{1}{(t_1 - t_2)} \ln\left(\frac{(p_2 - p_0)}{(p_1 - p_0)}\right) \quad (4)$$

where $p_2$ is the partial pressure of oxygen at time $t_2$. Thus κ may be determined without knowing the material and dimensional characteristics of the package. This allows determining the product of the often unknown diffusion constant and solubility coefficient for the packaging material, since the other constants and variables in Eqn. (2) are straightforward to measure/determine.

However, within the field of food packaging materials, it is customary to operate with the oxygen transmission rate (OTR) as a measure of the oxygen penetration into the package instead of the resulting oxygen concentration which is the outcome of Eqn. (3). The OTR is normally expressed as $dV_{Oxygen}/dt$, where the oxygen volume $V_{Oxygen}$ is referred to the pressure of the standard atmosphere. Thus, by derivating Eqn. (3) with time and employing the ideal gas law to substitute from dp/dt to $dV_{Oxygen}/dt$, the oxygen transmission rate can be given as:

$$\frac{dV_{Oxygen}}{dt} = \frac{V\kappa}{p_{atm}}(p_0 - p_1)e^{-\kappa(t-t_1)} \quad (5)$$

Note that Eqn. 4 and 5 (or its equivalence, Eqn. 3 and 4) constitutes an especially practical tool for predicting the oxygen penetration into food packages as a function of time, since all that is needed as input are two measurements of the actual oxygen concentration in the gas inside the package at two different times and the volume of the package. Also, since Eqn. 3 is a general theoretical expression for the partial pressure of oxygen inside a package (or volumetric flow of oxygen into the package, Eqn. 5) due to diffusion through the package walls which is based on the fundamental physics involved when oxygen molecules diffuses through a material, it will give a robust and reliable prediction valid for virtually any ambient condition the package may encounter as long as the ambient conditions are essentially stable during the measurements. This is a great advantage since expressions concerning mass diffusion will normally require knowledge of characteristic coefficients such as the diffusion constant. But the diffusion constant is usually very dependent upon the material characteristics of the package material in question and the external conditions such as temperature, air humidity etc, such that in practice, the diffusion constant is very difficult to obtain. Therefore, since Eqn. 3 (or Eqn. 5) is linked to the real world by just two measurements of the easy accessible partial pressure of oxygen inside the package, the inventive method becomes a practical and robust way of predicting the oxygen concentration as a function of time that can be performed at almost any condition. This includes even packages in temperatures below 0° C.

As mentioned, the commercially established methods for measuring OTR will normally measure the oxygen penetration through the barrier material in the case when one side of the material faces a gas stream with a constant oxygen content and the other side faces an oxygen free gas. The driving force for the diffusion process is therefore always at a maximum in the conventional method, in contrast to the inventive method of this invention where the diffusion process faces an increasing oxygen concentration on the inside of the package which results in a corresponding decrease in the driving force. In order to be able to compare OTR values as determined by the inventive method with conventional values, and which are the standard in the field of food packages, one should use the values for the initial period when there is no oxygen concentration within the package and the oxygen in the ambient air is exposed to an maximum driving force for penetrating the barrier material. That is, one should compare the OTR as determined at time $t_0$ when the partial pressure of the oxygen inside the package is zero. Time $t_0$ can be found by setting $t_1=t_0$ and $p(t_0)=0$ in Eqn. (3):

$$t_0 = t_1 - \frac{1}{\kappa}\ln\left(\frac{p_0}{p_0 - p_1}\right) \quad (6)$$

When inserting $t_0$ into Eqn. (5), the oxygen transmission rate at time zero can be given as:

$$\left.\frac{dV_{Oxygen}}{dt}\right|_{t=t_0} = \frac{p_0 V \kappa}{p_{atm}} \quad (7)$$

For food packages where the food is consuming all oxygen that enters the package (due to reactions with the food, e.g. microbial growth, colour changes in fresh and cured meats, oxidation of lipids and consequent rancidity, and senescence of fruit and vegetables), it is the oxygen transmission rate at time zero as given in Eqn. (7) that is the correct expression since there will be no significant build-up of a partial oxygen pressure in the gas inside the package.

The inventive method is based on exploiting the theoretical expressions for predicting the OTR into a package. That is, the inventive method can be summarised as follows:

determine the internal volume of the package, flush the package with sufficient amounts inert gas to ensure that the interior of the package is nearly free of the gaseous substance in question, allow the package to remain exposed to the ambient air/gas for a first time period under almost stable conditions, and measure the first concentration of the gaseous substance inside the package at the end of this first period, allow the package to remain exposed to ambient air for a second time period under the same stable ambient conditions as for the first period, and measure the second concentration of the gaseous substance inside the package at the end of this second period, employ the first and second measured gas concentrations in one or several of Eqns. (3–7) to predict the penetration rate of the gaseous substance into the package as a function of time.

The inventive method has an advantage over prior methods since it gives the penetration rate of a gaseous substance into a package for all times, regardless of the ambient conditions as long as they are fairly stable during the measurements. Conventional methods for measuring OTR are confined to standardised conditions which simulates an oxygen free package (maximum achievable driving force for the diffusion process). The inventive method can be applied for any type of food package at any condition they may face, including temperatures below 0° C. Also note that the inventive method does not require that the interior of the package at the beginning of the first period is absolutely free from the gaseous substance. All that is required is that the concentration inside the package is sufficiently low compared to the concentration outside the package that a diffusion process is emerging. In practice this means that the interior should only be rather low of the gaseous substance at the beginning of the measurements, and this gives a considerable ease in practising the inventive method since absolute removal of a gaseous substance is hard to achieve.

In general, one has that a diffusion process through a barrier material is initially unsteady, and the transient time before stable conditions are established is material dependent. One should therefore ensure that stable conditions are established before performing the first determination of the oxygen concentration inside the package. For the conventional and commercially established isostatic method, there is developed a standardised procedure for determining when the stable period begins. This procedure is described in Standard Specifications, section F1307-90 of the American Society for Testing and Specification of Materials (ASTM). In the case of determining OTR into food packages, it is recommended to employ the same initial time, $t_1$, for making the first determination of the partial oxygen pressure within the package when using the inventive method.

It is important that the package is sealed during testing and that it is being flushed with inert gas to ensure that the interior of the package is nearly free of oxygen or the gaseous substance in question. That is, one must also ensure that the equipment for taking out samples of the gas inside the package does not cause a leakage of ambient air/gas into the package. It is obvious for a skilled person that one may employ any known method for flushing the package and taking out gas samples as long as the interior of the package is not exposed to ambient air. All such known sample taking methods should therefore be considered as equivalent solutions to our preferred solution as given in the examples, and thereby incorporated in the invention.

Also, any conventional method for measuring the concentration of the gas in question inside the package can be employed, including for instance analysers that must have gas samples withdrawn from the interior of the package and analysers that can detect the gas concentration through the material wall. It is also envisioned analysers that withdraw a gas sample, performs the gas concentration determination and then re-injects the gas sample into the package.

In the case of applying analysers that require a withdrawn gas sample that is being subsequently discharged, it is preferred to employ analysers that are capable of detecting the gas concentration in a relatively small gas sample (in the order of 10 ml or less), since the predicted OTR-value is dependent upon the volume of the package (see Eqn. (5)). Thus a change of the package volume will induce an error in the estimate, and this error should be minimised by minimising the volume of the extracted gas sample.

LIST OF FIGURES

DETAILED DESCRIPTION OF THE INVENTION

The invention will be described in more detail under reference to the accompanying drawings and examples of preferred embodiments. However, these are only given for illustrative purposes and should therefore not be interpreted as limiting to the scope of the invention.

EXAMPLE 1

Predicting OTR in Food Packages

As mentioned, the costs associated with food package materials in the food industry are a vital competitive factor.

Thus, when investigating OTR in food packages, one should employ a sufficiently simple but still satisfactory accurate analysing equipment as possible in order to reduce costs. A preferred instrument is MOCON/Toray oxygen analyser LC-700F with a zirconium oxide cell (Modern Controls Inc, Minnesota, USA) with a system accuracy of ±2% in the interval 0–50% $O_2$ (with two decimals) and ±3% in the interval 0–0.5% $O_2$ (with three decimals). It is preferred to employ pure nitrogen gas as the inert gas since pure $N_2$ is relatively inexpensive and the ambient air is composed of 21% oxygen and the rest being mainly nitrogen, such that one obtains nearly real conditions during the measurements since pure $N_2$ almost resembles oxygen deprived air. The package should be flushed with sufficiently amounts of pure $N_2$ prior the measurements in order to ensure that the interior of the package is almost free of oxygen.

The MOCON/Toray oxygen analyser LC-700F requires that a gas sample from the interior of the package is taken out and inserted into the zirconium oxide cell. The gas sample is being discharged after the measurement. Thus a sample taking device that is sealing of the package during testing and sample taking is required. It is preferred to obtain this by penetrating the package wall with a hollow bolt which is threaded in both ends and equipped with a centre flange containing a sealing gasket. Then it may be air tight sealed onto the package by for instance firmly squeezing the package material between the flange with the sealing gasket by screwing on a retaining nut with another sealing gasket onto the inward protruding end of the bolt, such that the only escape route for gas inside the package is through the interior of the hollow bolt. Thus, if the hollow interior of the bolt is sealed off from the ambient air by for instance screwing on an endnut with a barrier septum onto the outward protruding end of the hollow bolt, one may take out gas samples from the interior of the package without breaking the sealing by inserting a needle of a syringe through the barrier septum.

Figure 1:
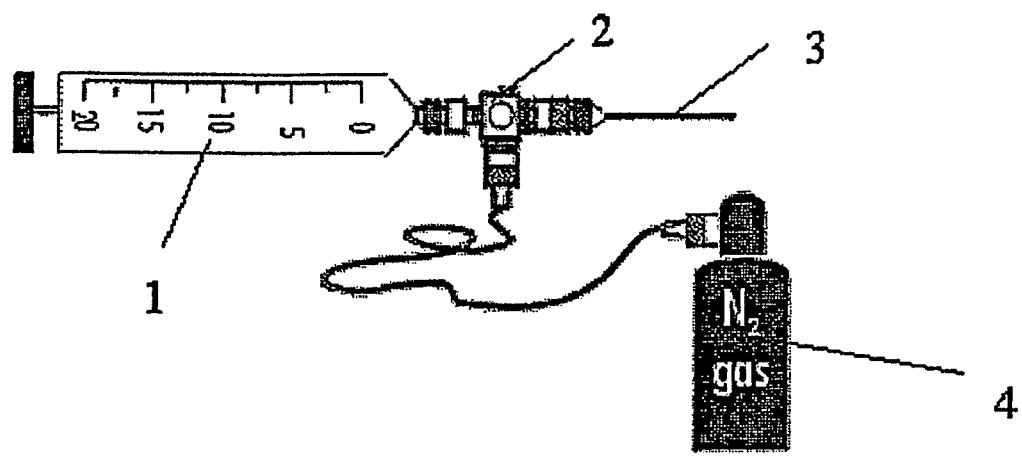
FIG. 1 illustrates one preferred embodiment of the device for taking out gas samples from packages.

It is preferred to compensate for the withdrawal of the gas sample by first inserting an exactly equal amount of the inert gas prior to the sample taking. An example of a preferred embodiment of a syringe for taking out an exact amount of gas is illustrated in FIG. 1. The syringe 1 is connected to a supply 4 of pure nitrogen and a needle 3 by a three-way valve 2. In this way, the syringe can be flushed with pure nitrogen before inserting the needle into the package through the sealing septum, and the syringe may be filled with a controllable amount of pure nitrogen gas that is to be injected into the package. Then the syringe can be filled with an exact equal amount of gas from the interior of the package, and the syringe with needle is withdrawn from the package and inserted into the oxygen analyser. Finally, the gas sample is injected in order to obtain the oxygen concentration of the sample.

Another advantage with the preferred embodiment is that in the case of a flexible package material, the needle syringe and barrier septum may be used to empty the package for gas and then inject an inert gas for several cycles in order to flush out virtually all oxygen inside the package.

Figure 2:
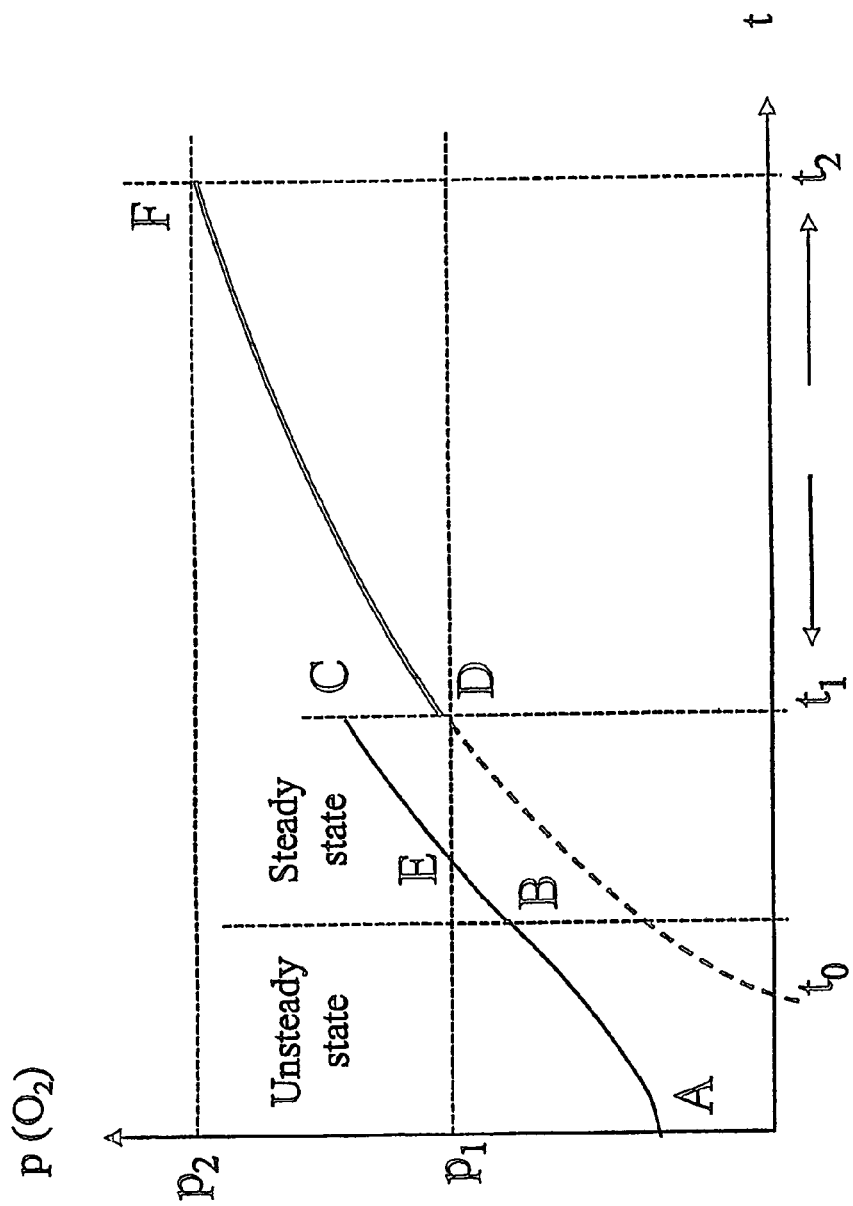
FIG. 2 is a graph illustrating one measurement procedure according to the invention.

A typical measuring procedure is illustrated schematically in FIG. 2, and may be described as follows:

The package was flushed through the open hollow bolt with nitrogen for one minute until the oxygen level was close to zero, marked with point A in FIG. 2. After flushing, the sampling port (hollow bolt) were sealed by mounting on the endnut containing the septum barrier. The test package was then conditioned in ambient air (21% oxygen) for 18–24 hours (corresponds to the conditioning time employed in the conventional methods). During this period of time the packages normally will establish steady state condition, marked with B in FIG. 2.

At the point marked C in FIG. 2, 10 ml $N_2$ was injected into the test package with the specially designed syringe. The syringe plunger was pulled up and pushed down 2–3 times in order to mix the gas inside the package. The 10 ml of $N_2$ was injected to compensate for the volume change when removing 10 ml of the total volume in next step. Injecting 10 ml $N_2$ into the package lowers the $O_2$-concentration, which drops from point C to point D in FIG. 2.

At point D, a sample of 10 ml gas was withdrawn and injected into the oxygen analyser. The measured partial pressure of $O_2$ in the withdrawn gas sample was recorded as oxygen level $p_1$ at time $t_1$. After sampling, as shown in FIG. 2, the ingress rate changes from the rate $R_c$ at C back to the rate $R_D$ at D, which is equal to the rate $R_E$ at E.

At the point marked F in FIG. 2, the final sample of 10 ml gas was withdrawn and injected into the oxygen analyser. Time $t_2$ will typically be in the order of 3–6 days after $t_1$. The obtained oxygen concentration was recorded as $p_2$ at time $t_2$.

Finally, the transmission rate of oxygen into the whole package, expressed as ml $O_2$/day, was then calculated by converting the measured oxygen concentrations $p_1$ and $p_2$ to units ml $O_2$/day, and then employing Eqns. (4) and (5) to give the curve marked with the broken line between time $t_0$ and $t_1$, and the solid bolded curve between time $t_1$ and $t_2$ (the curve runs between points D and F, respectively).

The procedure as shown in FIG. 2 combined by using the exponential equation has the following advantages:

The packages do not have to be totally free from oxygen from the beginning at A.

The change in ingress rate due to step C and D is taken into account, because the initial $O_2$-concentration is recorded after injecting 10 ml nitrogen (D).

The OTR-value can easily be calculated at time $t_0$ by employing Eqn. (7), which was the time where the oxygen pressure was zero when a steady state process is simulated. This will be the most correct value when comparing with conventionally obtained OTR-values when measured by the isostatic method.

The Toray instrument was always calibrated before starting the measurement of each series of initial or final $O_2$-concentration. The instrument was calibrated towards air in the upper part of the scale and towards a reference gas containing 0.21% $O_2$ in $N_2$ in the lower part of the scale.

EXAMPLE 2

In order to make a practical tool for the manufacturers and/or consumers of food package materials, it is envisioned that the inventive method can be employed to make screening tests for a packaging material at various conditions expected to be found during handling of the food package in commercial use, and employ these tests to produce graphs over the OTR-value as a function of time for a set of expected ambient conditions.

These graphs may constitute a very useful instrument for performing spot tests of package materials, since they provide a data bank which may be employed to check whether new packages behave like the packages employed in the screening tests. That is, screening tests of a certain packaging material at the conditions found in food stores according to the inventive method may be used to produce graphs (such as the graph running from $t_0$ to F in FIG. 2) of the oxygen transmission rate as a function of time (for an empty package, no oxygen being consumed) at these conditions. Then, e.g. a manufacturer etc. of the food packaging material can perform spot testing by simply take out an empty package from the production line, let it stay for a certain time period at the expected condition, and then take out a gas sample and measure the oxygen concentration inside the package. This value will immediately tell whether the late package behaved like the packages employed for the screening tests, since the spot test oxygen concentration should be lying on the screen test graph if the OTR-values are equal.

Note that in this case, it is only necessary to perform one single determination (measurement) of the oxygen concentration inside the package. Thus there is no need for applying a sample taking device (such as the hollow bolt with a septum barrier as in example 1) on the package which is sealing the package. All that is required is a device that can withdraw a gas sample and inject it into the oxygen analyser. Thus the package can be discharged afterwards (since there is no need for taking two gas samples).

It is envisioned that this device may be in the form of a pocket sized integrated unit containing a penetration device, an oxygen analyser, and means for displaying the determined oxygen concentration. It may also contain means for storing the screening tests and software that performs the comparison between the spot test and screening tests, in order to make the apparatus very practical in use for large series of spot tests.

This device will therefore constitute a very simple and relatively inexpensive way of obtaining spot testing in the food package industry. Today, the conventional methods for measuring the OTR are so cumbersome and expensive, that regularly spot testing of package materials are not practically feasible.

EXAMPLE 3

Verification of the Inventive Method

In order to verify the inventive method for measuring the oxygen penetration into packages, five different barrier materials were measured by employing a conventional Ox-Tran apparatus and the inventive method as described in example 1. The packages and materials were: 1) 300 ml polyvinylchloride (PVC)-bottles (Grathwol AS, Glostrup, Denmark); 2) 960 ml thermoformed trays; top web: a laminate of 20 µm polyamide (PA) and 60 µm polyethylene (PE), base web: a laminate of 530–550 µm PVC and 45 µm PE with 3% ethylenevinylacetate (EVA) (Dixie Union, Germany); 3) 540 ml high density polyethylene (HDPE)-bottles (MG Plast AS, Moss, Norway); 4) 500 ml polypropylene (PP)-bottles (MG Plast AS, Moss, Norway); and 5) 175 ml PS-cup (Dynopack Stjørdal, Norway). It was anticipated that the selected packages would have different OTR values within the range of the Ox-Tran equipment and would be non-hygroscopic (minimal influence of variation in relative humidity in the environment).

Packages for both Ox-Tran and the inventive measurements were conditioned in the same room, and the temperature and relative humidity in the room was registered by a Novasina ms1 Hygro Measuring System (Defensor AG, CH-8808 Pfäffikon SZ) during the experimental period. The temperature in the conditioning room varied from 19.3 to 23° C. and the relative humidity from 14 to 23%. Four identical packages of each type were analysed on the Ox-Tran equipment, and a minimum of four were run by the inventive method with two sets of elapsed times between measurement of initial and final $O_2$-concentrations. The experimental data were evaluated statistically by a two-way ANOVA and by linear regression (Minitab 12).

The Ox-Tran measurements were performed using a Mocon Ox-tran 100 twin (Modern Controls Inc, Minnesota, USA). Standard specifications from designation F 1307-90 of the American Society for Testing and Materials (ASTM) were applied.

The permeant was oxygen in ambient air; the gradient was thus 0,21 atm. The packages were conditioned for 18–24 hours before measuring the Ox-Tran-values.

The results are summarised in Table 1. From the table, it is evident that the inventive method gave equal OTR-values compared to the Ox-Tran method within the entire range of OTR values for the five different types of whole packages used in the experiment. The accuracy of the inventive method was satisfactory despite

TABLE 1

Comparison between oxygen transmission rate for five packages obtained by an Ox-Tran instrument and the inventive method.

| | Oxygen transmission rate [a] | | |
|---|---|---|---|
| Package | Ox-Tran Mean + SD | Δt [b] | Inventive method Mean ± SD |
| PVC-bottle | 0.06 + 0.01 | 3 | 0.06 + 0.02 |
| Thermoformed tray | 0.23 + 0.01 | 3 | 0.26 + 0.04 |
| HDPE-bottle | 0.43 + 0.02 | 1 | 0.43 + 0.02 |
| PP-bottle | 1.00 + 0.04 | 1 | 1.00 + 0.03 |
| PS-cup | 1.48 + 0.06 | 1 | 1.48 + 0.07 |
| Repeatability of the inventive method: | | | |
| (HDPE-bottle [c]): | | 3 | 0.38 + 0.01 |

[a] ml $O_2$/day
[b] elapsed time = days between measurement of initial and final $O_2$-concentration
[c] this HDPE-bottle had a different production number than the HDPE-bottles above that the standard deviation can be expected to be slightly higher when using the inventive method compared to the Ox-Tran method. The inventive method can therefore be considered to be a reliable and precise alternative method to the Ox-Tran-method for measuring OTR of whole packages. The equipment required in the inventive method is relatively inexpensive and the capacity is high, and the method is flexible with respect to the range of OTR-values and to package size.

Even though the inventive method has been described as a method for determining the oxygen penetration into food packages, it is obvious for a skilled person that the inventive method can be applied for determining penetration of any other specie that possibly could diffuse through a material, by simply substitute the nitrogen gas (if necessary) and apply an appropriate inert gas and analysing equipment that is able to detect the actual specie. It is also fairly obvious that this method is far from constricted to food packages, but can be employed for all types of packages of any size, shape, material, intended use etc.

REFERENCES

1. Demorest R L. *J. Plastic Film & Sheeting.* 1992; 8: 109–123.

Larsen H., Kohler A., and Magnus E. M. (2000), "Ambient Oxygen Ingress Rate method—an alternative method to Ox-Tran for measuring oxygen transmission rate of whole packages", *Technol. Sci,* 13: 233–241.

What is claimed is:

1. Method for determining the penetration rate of a gaseous substance into a closed package made of a package material, characterised in that the method comprises:
   flushing the package with an inert gas for a sufficiently period to ensure that the interior of the package contains only small amounts of the gaseous substance, and then seal off the package against the ambient atmosphere,
   exposing the closed package to ambient atmosphere containing a known quantity of the gaseous substance for a first specified time period,
   when reaching the end of the first time period, determine a first concentration of the gaseous substance within the package at the end of the first time period, allowing the package to be exposed to the ambient gas for a second time period, when reaching the end of the second time period, determine a second concentration of the gaseous substance within the package at the end of the second time period, and employ the two measured concentrations of the gaseous substance in the equation $$\frac{d V_{Oxygen}}{d t} = \frac{V \kappa}{p_{otm}}(p_0 - p_1)e^{-\kappa(t-t_1)}$$

to predict the penetration rate of the gaseous substance into the closed package as a function of time.

2. Method according to claim 1, characterised in that the gaseous substance is oxygen, and that the inert gas is pure nitrogen.

3. Method for performing spot tests to evaluate the penetration rates of a oxygen into an empty closed package in relation to a reference value, characterised in that the method comprises: 1) in the case where the reference value is not available:

establish a set of reference values of the oxygen transmission rate for all times by performing a series of screening tests of packages made of the same material and which has equal dimensions as the said package for a set of conditions the package is expected to meet in commercial handling by employing the method as given in claim 2, except that the oxygen transmission rates should be given as the resulting oxygen concentration inside the package by employing equation:

$$p(t) = p_0 + (p_1 - p_0)e^{-\kappa(t-t_1)}$$

perform spot testing of the said package, where the spot testing involves to first flush the empty package with inert gas such that practically all of the said gaseous substance is removed, leaving the package to be exposed to the ambient atmosphere for a certain time period, and then determine the oxygen concentration of the said empty package, and compare the determined said oxygen concentration after the time period with the reference value to determine whether to oxygen transmission rates of the said package are equal to the reference packages, or 2) in the case reference values are available:

perform spot testing of the said package, where the spot testing involves to first flush the empty package with inert gas such that practically all of the said gaseous substance is removed, leaving the package to be exposed to the ambient atmosphere for a certain time period, and then determine the oxygen concentration of the said empty package, and compare the determined said oxygen concentration after the time period with the reference value to determine whether the oxygen transmission rates of the said package are equal to the reference packages.

4. Method for determining the penetration rate of a oxygen into a closed package, characterised in that the method comprises:

inserting means for withdrawing a gas sample from the package in such a manner that the interior of the package is not exposed to ambient gas (outside the package), flushing the package with pure nitrogen for a sufficiently period to ensure that the interior of the package contains only little oxygen, exposing the closed package to ambient for a first specified time period, when reaching the end of the first time period, inserting a specified amount of pure nitrogen gas into the package and allowing the inserted nitrogen to mix homogeneously with the gas inside the package, when the gas inside the package is homogeneously mixed, withdraw a gas sample with exactly the same volume as the inserted nitrogen, and analyse the gas sample from the interior in order to determine the concentration of the oxygen in the sample after the first time period, allowing the package to be exposed to the ambient air for a second time period, when reaching the end of the second time period, withdraw another sample of the gas from the inside of the package and analyse it in order to determine the oxygen concentration in the sample after the second time period, and insert the two measured oxygen concentrations in equation $$\frac{d V_{Oxygen}}{d t} = \frac{V \kappa}{p_{otm}}(p_0 - p_1)e^{-\kappa(t-t_1)}$$

and/or equation $$\left.\frac{d V_{Oxygen}}{d t}\right|_{t=t_0} = \frac{p_0 V \kappa}{p_{otm}}$$

to predict the oxygen transmission rate into the package.

5. Method according to any of claims 1,2,3 or 4, characterised in that the package is a food package or a pharmaceutical package.

6. Device for determining spot tests of the penetration rate of a gaseous substance into a closed package by using the method according to any of claims 1,2,3 or 4, where the package that is being tested is initially flushed with inert gas, sealed, and then exposed to the ambient atmosphere for a certain time period, characterised in that it comprises:

an injector which is capable of withdrawing gas samples from the interior of the package, a gas analyser that is in communication with the injector and which determines the concentration of the gaseous substance, computer hardware that is in communication with the gas analyser, and which is able to memorise a set of predetermined reference values of the transmission rates as a function of time for different ambient conditions, computer software incorporated into the computer hardware that is able to register the measured gas concentration directly from the gas analyser and then compare it with the reference values, and displaying means that is able to display the comparison between the actually determined and the reference value of the gas concentration.

7. Device according to claim 6, characterised in that the gaseous substance is oxygen, and that the inert gas is pure nitrogen.

* * * * *